(12) United States Patent
Olsen et al.

(10) Patent No.: US 6,701,926 B2
(45) Date of Patent: Mar. 9, 2004

(54) BREATHING ASSISTANCE APPARATUS

(75) Inventors: Gregory James Olsen, Auckland (NZ); Martin Leckie, Auckland (NZ); Neil Prime, Auckland (NZ); Lewis George Gradon, Auckland (NZ); Nicholas Charles Alan Smith, Auckland (NZ); Alastair Edwin McAuley, Auckland (NZ); Mark Joseph Haycock, Auckland (NZ); Chris Earl Nightingale, Auckland (NZ); Geoffrey Mark Shaw, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/278,317

(22) Filed: Oct. 23, 2002

(65) Prior Publication Data

US 2003/0111080 A1 Jun. 19, 2003

Related U.S. Application Data

(63) Continuation-in-part of application No. 10/072,271, filed on Feb. 7, 2002, which is a continuation-in-part of application No. 09/881,633, filed on Jun. 14, 2001.

(30) Foreign Application Priority Data

| | | | |
|---|---|---|---|
| Jun. 14, 2000 | (NZ) | | 505154 |
| Jun. 14, 2000 | (NZ) | | 505155 |
| Jun. 14, 2000 | (NZ) | | 505156 |
| Nov. 16, 2000 | (NZ) | | 508218 |
| Nov. 16, 2000 | (NZ) | | 508219 |
| Nov. 27, 2000 | (NZ) | | 508433 |
| Dec. 20, 2000 | (NZ) | | 509039 |
| Sep. 13, 2001 | (NZ) | | 514184 |
| Oct. 23, 2001 | (NZ) | | 514972 |

(51) Int. Cl.$^7$ ............................................. A62B 18/08
(52) U.S. Cl. ................................................. 128/207.11
(58) Field of Search ....................... 128/206.13, 206.27, 128/207.11, 207.17, 206.12, 206.18, 206.21, 206.28, 207.13

(56) References Cited

U.S. PATENT DOCUMENTS

| | | | |
|---|---|---|---|
| 2,414,405 A | | 1/1947 | Bierman et al. |
| 2,837,090 A | | 6/1958 | Bloom et al. |
| 5,662,101 A | * | 9/1997 | Ogden et al. .......... 128/205.25 |
| 5,832,918 A | | 11/1998 | Pantino |
| 5,975,079 A | | 11/1999 | Hellings et al. |
| 6,044,844 A | * | 4/2000 | Kwok et al. ........... 128/207.11 |

* cited by examiner

*Primary Examiner*—Henry Bennett
*Assistant Examiner*—Malik N. Drake
(74) *Attorney, Agent, or Firm*—Trexler, Bushnell, Giangiorgi, Blackstone & Marr, Ltd.

(57) ABSTRACT

A improved interface is disclosed for delivering CPAP therapy to patients. The interface has a sliding engagement to the headgear. The sliding engagement allows substantial relative lateral movement eg: when face is distorted from sleeping on side, while still providing adequate compressive force to avoid side leakage. The sliding engagement also allows easy release from the headgear.

22 Claims, 19 Drawing Sheets

BREATHING ASSISTANCE APPARATUS

This application is a Continuation-In-Part application of U.S. patent application Ser. No. 10/072,271 filed on Feb. 7, 2002, which is a Continuation-In-Part application of U.S. patent application Ser. No. 09/881,633 filed on Jun. 14, 2001, now allowed.

FIELD OF INVENTION

This invention relates to delivery of respiratory gases particularly though not solely to patient interfaces for providing gases to patients requiring respiratory therapy.

BACKGROUND OF THE INVENTION

In the art of respiration devices, there are well known a variety of patient interfaces which cover the nose and/or mouth of a human user in order to provide a continuous seal around the nasal and/or oral areas of the face such that gas may be provided at positive pressure for consumption by the user. The uses for such interfaces range from high altitude breathing (i.e., aviation applications) to mining and fire fighting applications, to various medical diagnostic and therapeutic applications.

One requisite of such respiratory interfaces has been that they provide an effective seal against the user's face to prevent leakage of the gas being supplied. Commonly, in prior configurations, a good interface-to-ice seal has been attained in many instances only with considerable discomfort for the user. This problem is most crucial in those applications, especially medical applications, which require the user to wear such an interface continuously for hours or perhaps even days. In such situations, the user will not tolerate the interface for long durations and optimum therapeutic or diagnostic objectives thus will not be achieved, or will be achieved with great difficulty and considerable user discomfort.

In common with prior art designs, is an inability to seal effectively when the user's face becomes distorted. For example, as shown in the prior art mask of FIG. 1 when the user 300 is sleeping on his or her side, one side 302 of the headgear tends to be pulled tight while the other side 304 tends to be loose. This causes the axis of the mask 306 to be twisted with respect to the axis of the head 308—due to the net torque from the headgear—resulting in leakage 310 on one side. The user 300 sleeping on his or her side may also distort the facial contours around he nasal area 312 and may lead to further leakage.

SUMMARY OF INVENTION

It is an object of the present invention to provide an interface which goes some way to overcoming the above-mentioned disadvantages in the prior art or which will at least provide the industry with a useful choice.

It is a further object of the present invention to provide an interface which is capable of providing an effective seal against the user's skin but which does not exert undue pressure on any part of the user's face.

A still further object of the present invention is to provide an interface which can be produced at lower cost than current designs.

Accordingly in a first aspect the present invention consists in a device for delivering a supply of gases to a user comprising or including:

a patient interface, adapted to be in fluid communication with a supply of gases, and adapted to provide a substantially sealed flow path for said flow of gases to a user in at least a correct orientation and position on a user, headgear adapted to attach to or around the head of a user, a sliding connection between to said patient interface, and wherein said sliding connection includes a sliding connection to said headgear.

Preferably said sliding connection comprises a loop adapted to slide on, through, with or adjacent said interface and adapted to slide on, through, with or adjacent said headgear.

Preferably said patient interface is a mask.
Preferably said patient interface is a nasal mask.
Preferably said patient interface is a full face mask.
Preferably said mask comprises or includes a body portion having an inlet receiving said supply of gases, and sealing means attached to or integrated with said body portion said sealing means adapted to seal against the facial contours of said user.

Preferably said sliding connection adapted to allow said headgear substantial movement with respect to said mask, while still providing compressive force on said sealing means to ensure said supply of gases is delivered to said user without significant leakage.

Preferably said sliding connection is connected to said interface at at last two points.

Preferably said loop comprises a continuous looped nylon filament.

Preferably said patient interface is a nasal cannula.
Preferably said patient interface is a mouthpiece.
Preferably said patient interface is an endotracheal tube.

In a second aspect the present invention consists in CPAP system for delivering gases to a user with a pressurised source of gases, a conduit in fluid communication with said pressurised source adapted to convey said gases, a patient interface in fluid communication with said conduit in use delivering said gases to said user, and headgear attaching said interface with said user the improvement comprising that said patient interface adapted to sliding engage with said headgear, to ensure said supply of gases is delivered to a user without significant leakage.

Preferably the improvement further comprising that said system further comprises a humidifier to variably humidify said gases.

In a third aspect the present invention consists in a device for delivering a supply of gases to a user comprising or including:

a patient interface, adapted to be in fluid communication with a supply of gases, and adapted to provide a substantially sealed flow path for said flow of gases to a user in at least a correct orientation and position on a user, and headgear attached to the head of a user, and at least a partial loop adapted to pass across the face of a user restraining movement of said interface with respect to said headgear.

Preferably said loop adapted to pass over and slidingly engage with said interface.

Preferably said loop adapted to pass at least partially through and slidingly engage with said interface.

Preferably said loop adapted to slidingly engage with said headgear.

In a fourth aspect the present invention consists in a mask which includes a rigid or semi rigid shell provided with a support harness for securing the mask over a user's face, and a flexible seal; the shell being provided with inlet means for a gas supply and a mounting for an exhaust valve; the flexible seal being a push fit inside the shell and dimensioned and arranged such that when pressurized gas is supplied through the inlet means, the seal is pushed outwards against the interior of the mask and against the user's face.

Preferably the support harness comprises a loop of low friction material which can slide freely through channels formed in the shell and relative to straps provided for securing the mask around a user's head.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the field of patient interfaces for use in respiratory therapy. In particular an interface is described which is more comfortable for the user to wear and reduces the side leakage as compared with interfaces of the prior art. It will be appreciated that while a mask is described in the preferred embodiment, the present invention can be used in respiratory care generally or with a ventilator but will now be described below with reference to use in a humidified CPAP system. It will be appreciated the present invention could equally be used with any form of positive pressure respiratory therapy.

Figure 3:
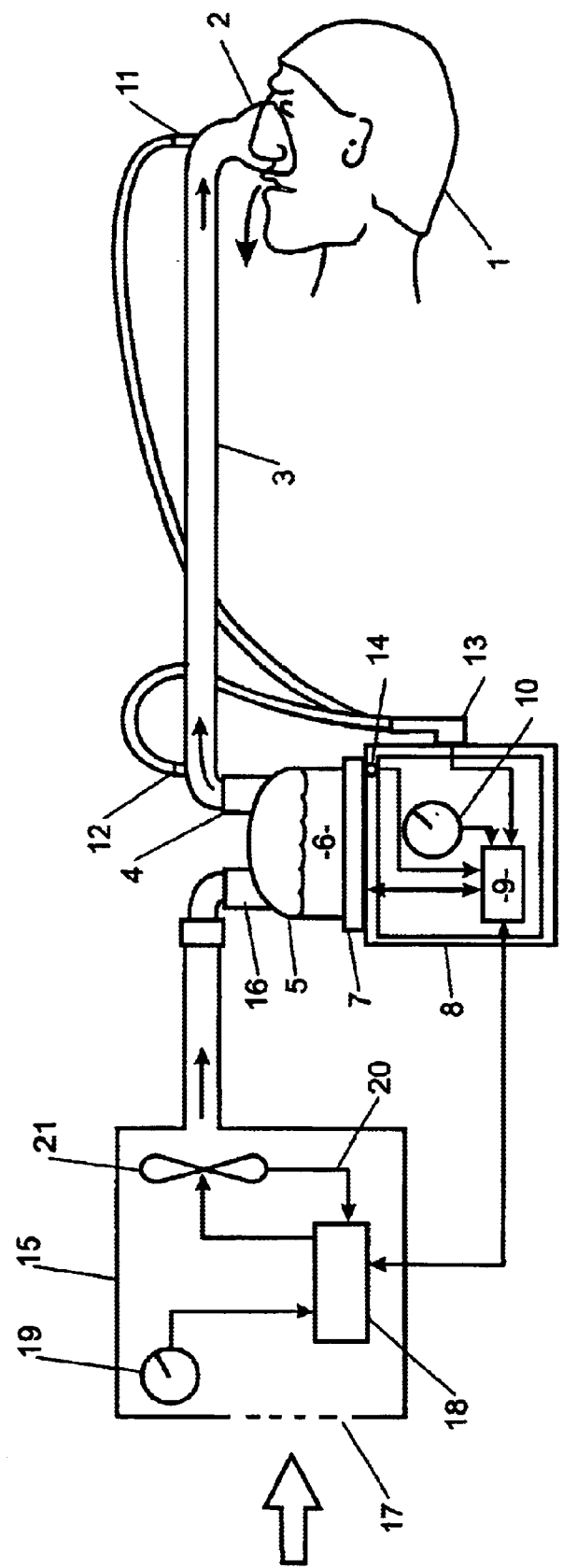
FIG. 3 is a block diagram of a humidified continuous positive airway pressure (CPAP system) as might be used in conjunction with the present invention.

With reference to FIG. 3 a humidified Continuous Positive Airway Pressure (CPAP) system is shown in which a patient 1 is receiving humidified and pressurised gases through a nasal mask 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 3.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 4:
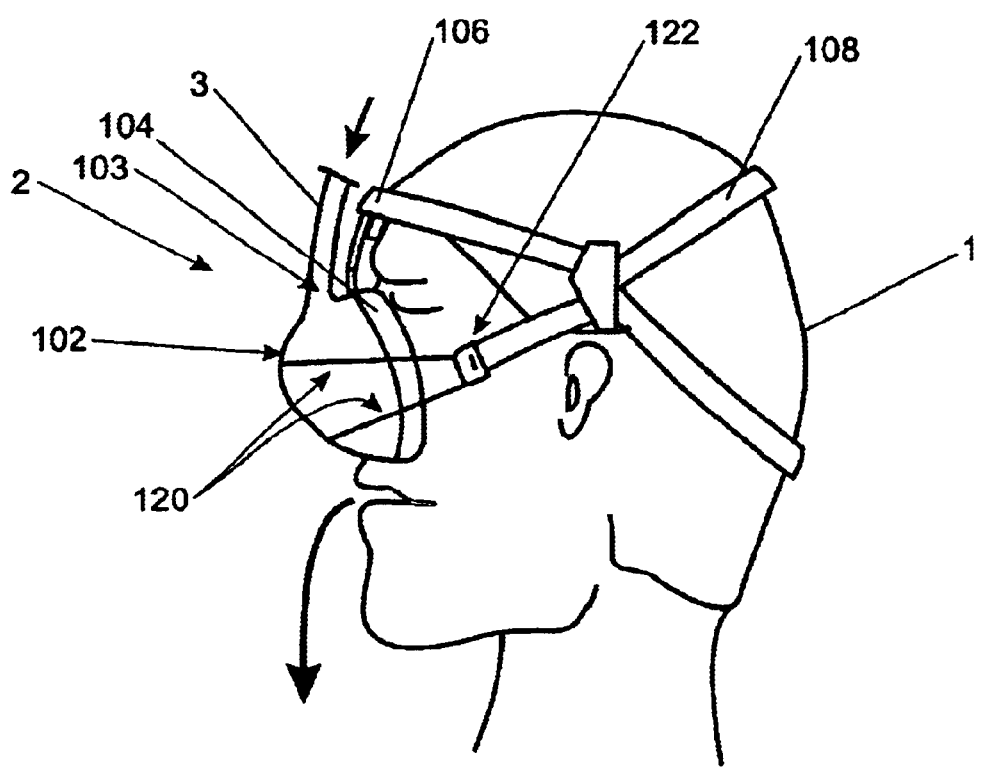
FIG. 4 is an illustration of the mask in use according to the preferred embodiment of the present invention.

Referring to FIG. 4 the nasal mask, according to the preferred embodiment of the present invention, is shown in detail. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is know in the art.

Mask Headgear

Figure 5:
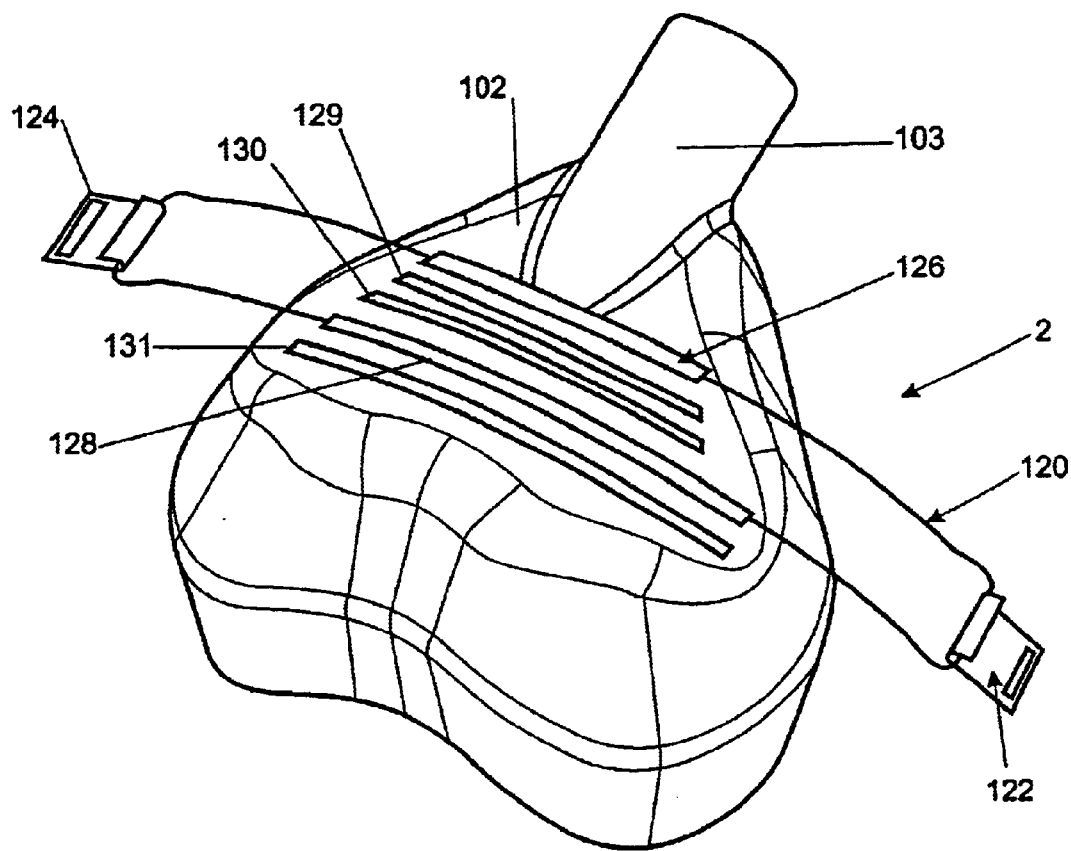
FIG. 5 is a front view of the mask illustrating the headgear securement to the mask.

Referring now to FIGS. 4 and 5 the headgear 108 is shown connected to the hollow body 102. Rather than traditional fixed or adjustable attachments the present invention utilises a sliding engagement between the headgear 108 and the hollow body 102. This is achieved in one embodiment with a loop 120, sliding through harnessing clips 122, 124 on either side of the headgear 108 and sliding over the top of the hollow body 102. The loop 120 is sliding engaged with guides 126, 128 mounted on the top surface of the hollow body 102. The guides constrain the loop 120 but allow it to slide in and out, meaning the headgear 108 can move horizontally and vertically, independently of the hollow body 102.

The advantage to this is as the face is contorted during various sleeping positions the headgear is able to move with the changes in position while the mask is left in the correct position on the nose of the user and an effective seal is maintained.

Additional guides 129, 130, 131 allow the user to adjust position of loop 120, giving ability to get different pressure on the seal depending on loop 120 position.

To further ensure user comfort and effective pressure on the mask cushion 104, the headgear 108 may be constructed either using two straps running around the back of the user's head as shown in FIG. 4 or with a partial skull cap or any other configurations as are known in the art In this case the straps or partial skull cap would be constructed using neoprene but may also be constructed using any material as is known in the art which will be comfortable for the user.

Figure 6:
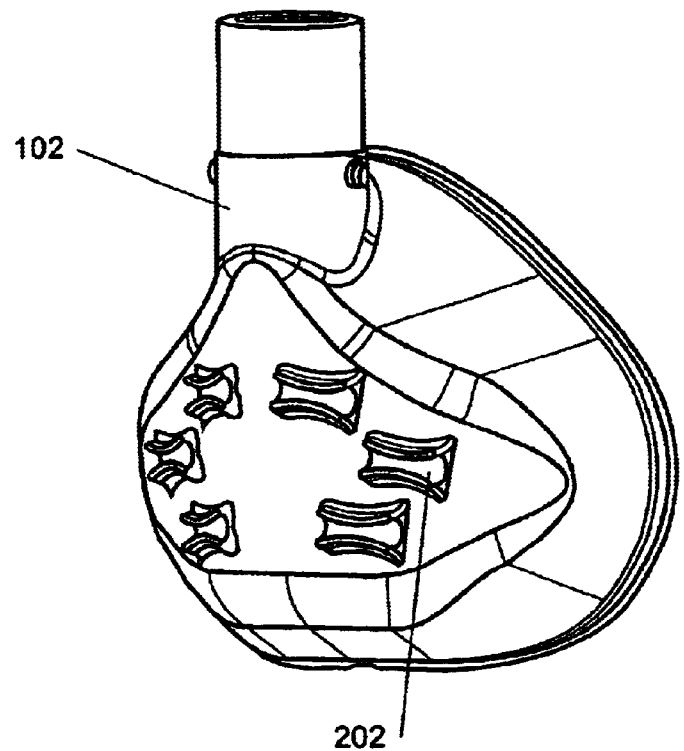
FIG. 6 is a perspective view of the mask showing multiple engaging clips.
Figure 7:
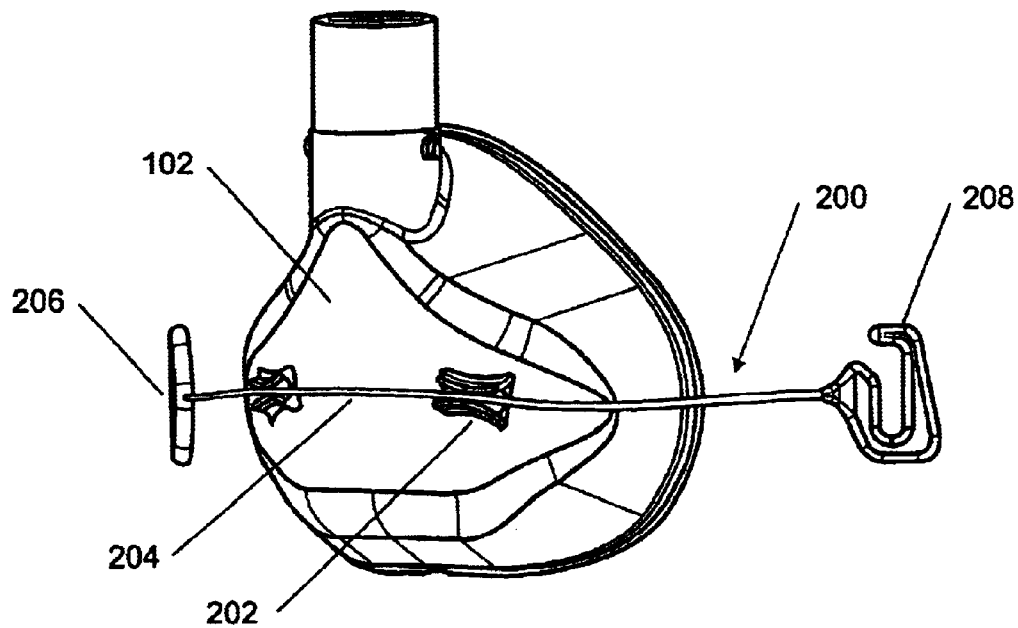
FIG. 7 is a perspective view of the mask showing the sliding strap clipped in place.
Figure 8:
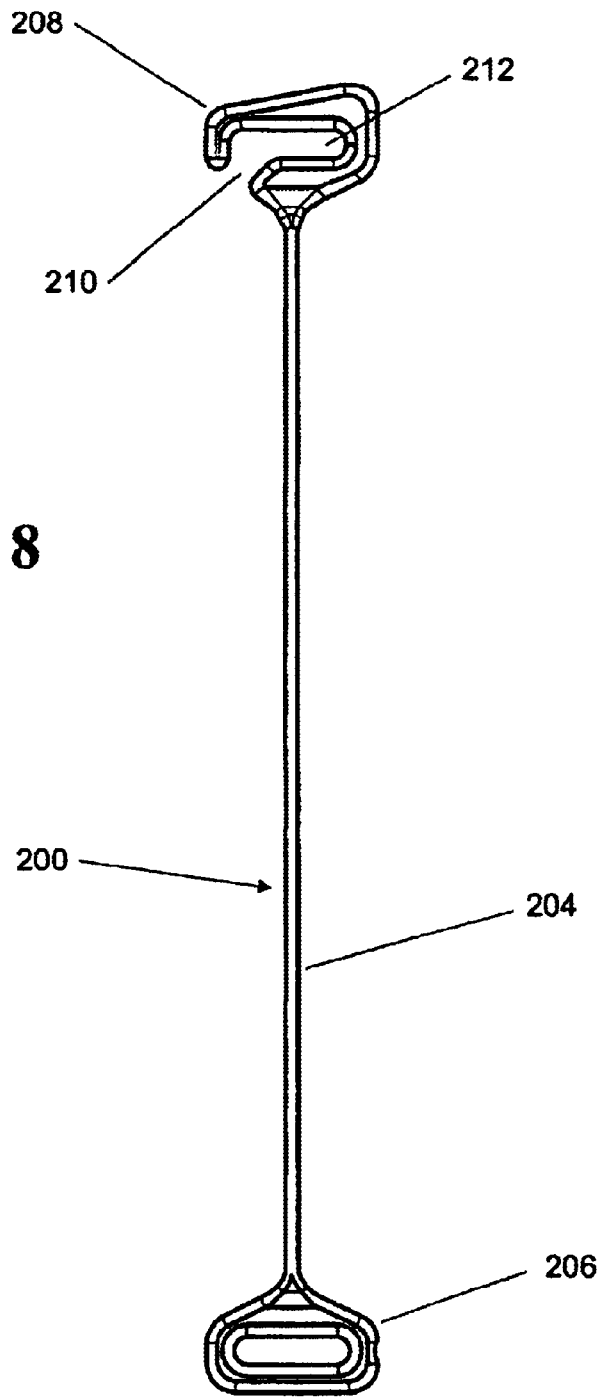
FIG. 8 is a side view of the sliding strap.

In a further embodiment shown in FIGS. 6, 7 and 8 the present invention is illustrated using a sliding strap to attach the headgear 108 to the hollow body 102. The strap 200, shown in FIG. 8 in isolation, is constructed of polyacetal (Delrin 500P NC010) using injection moulding techniques to give a polished finish. This material, similar to other nylon based derivatives, with its polished finish has a particularly low friction co-efficient, and therefore slides with respect to the hollow body 102 with very little resistance.

As shown in FIG. 6, the hollow body 102 includes a number of engaging clips 202, in use the sliding strap 200 snaps into place into the engaging clips 202 and can only be removed therefrom using a substantial force. This means that with any normal use the sliding strap 200 will stay retained within We engaging clips 202. It will also be appreciated from FIG. 6 that a number of clips are so provided, in order to allow pressure from different angles for different face shapes.

As shown in FIG. 8 the sliding strap includes a midsection 204 intended to reciprocate with the engaging clips 202, terminated at each end by loops 206, 208 which attach to the headgear. The first loop 206 is a full loop through which the headgear 108 is permanently attached with for example, a strap which is formed of VELCRO® material. The loop 208 at the other end, is only a partial loop 210 designed so that a strap or loop from the headgear 108 can be easily slipped in or out of the open section 212 to allow easy removal and attachment of the mask.

In a further alternative the sliding loop or strap could form a continuous portion of the headgear. Other variations of the sliding connection are possible, for example a clip or knob in the loop or strap could slide withing slots in the mask body.

Figure 1:
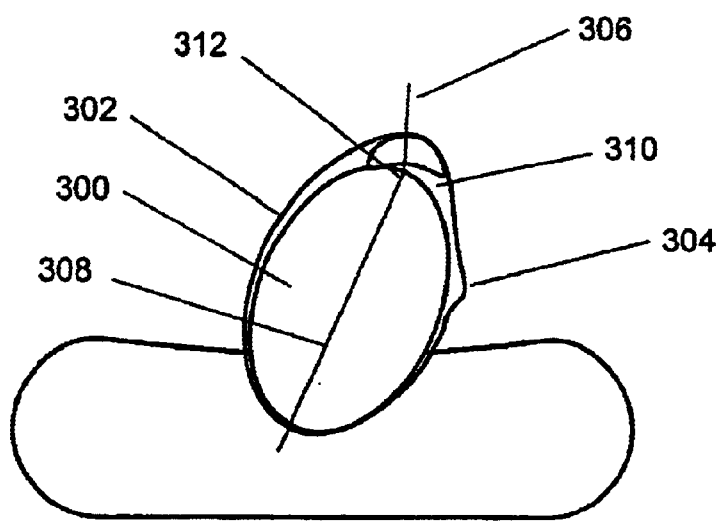
FIG. 1 is a plan view of a prior art mask illustrating side leak.
Figure 2:
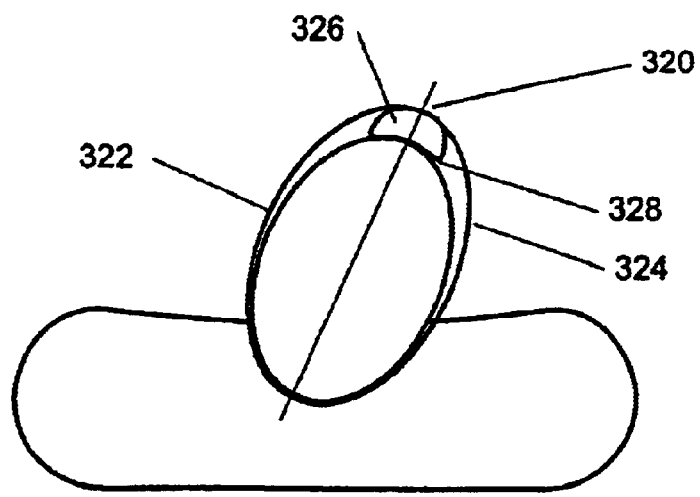
FIG. 2 is a plan view of a mask according to the preferred embodiment of the present invention.

It will be appreciated that in all embodiments of the present invention the attachment from the headgear to the mask is designed to slide with the lowest possible friction while sill ensuring adequate direct force on the mask cushion to the user's face. As shown in FIG. 2 the sliding connection 320 of the present invention allows the headgear 322,324 to provide even force on both sides of the mask 326. This avoids placing a torque on the mask and consequent mask twisting, which minimises mask leaks from the seal to the face 328.

Nasal Cannula

It will be appreciated that the present invention may be equally applied to any patient interface for delivery gases to a user.

Figure 9:
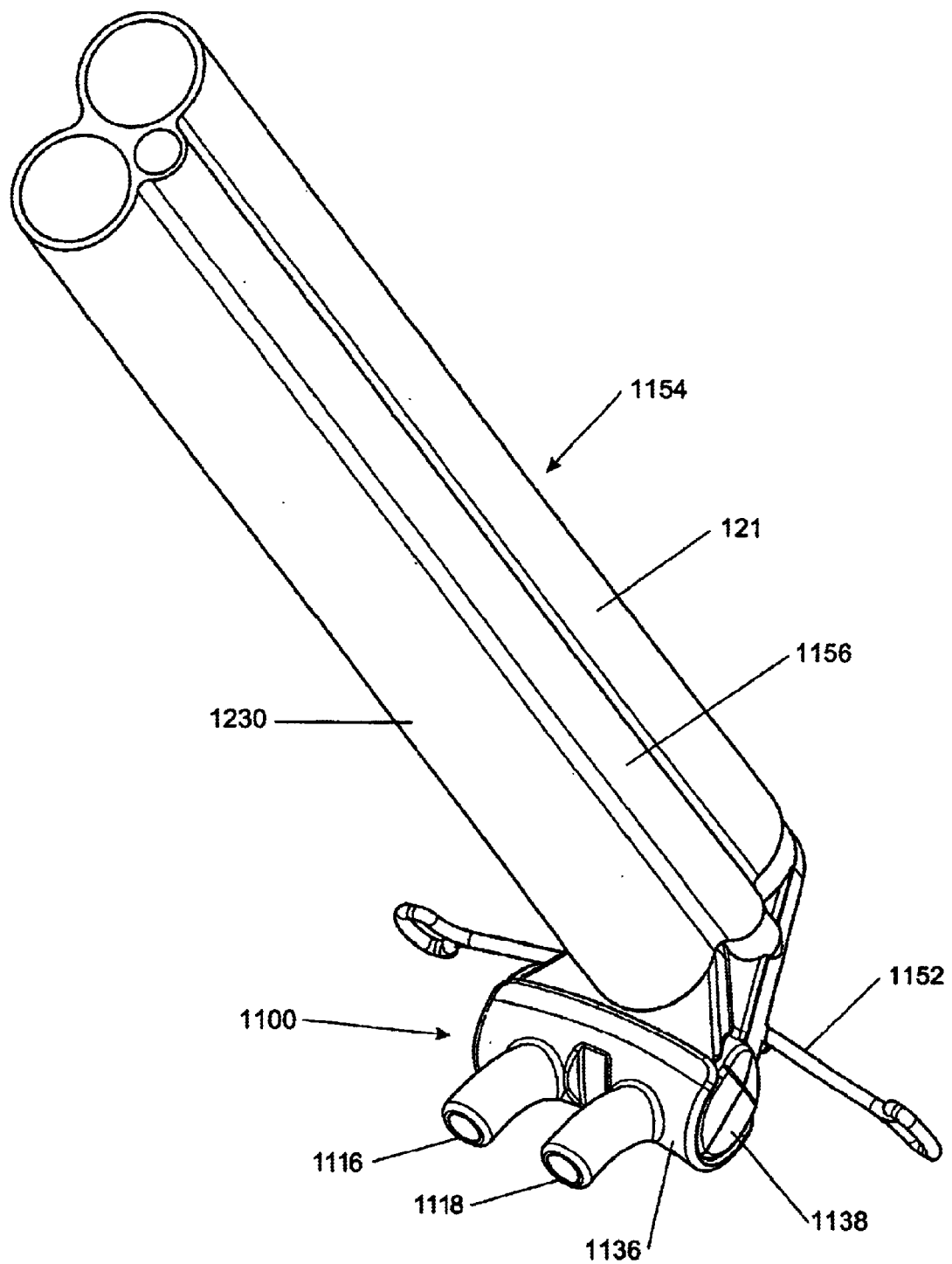
FIG. 9 is a perspective view of the cannula with the sliding strap
Figure 10:
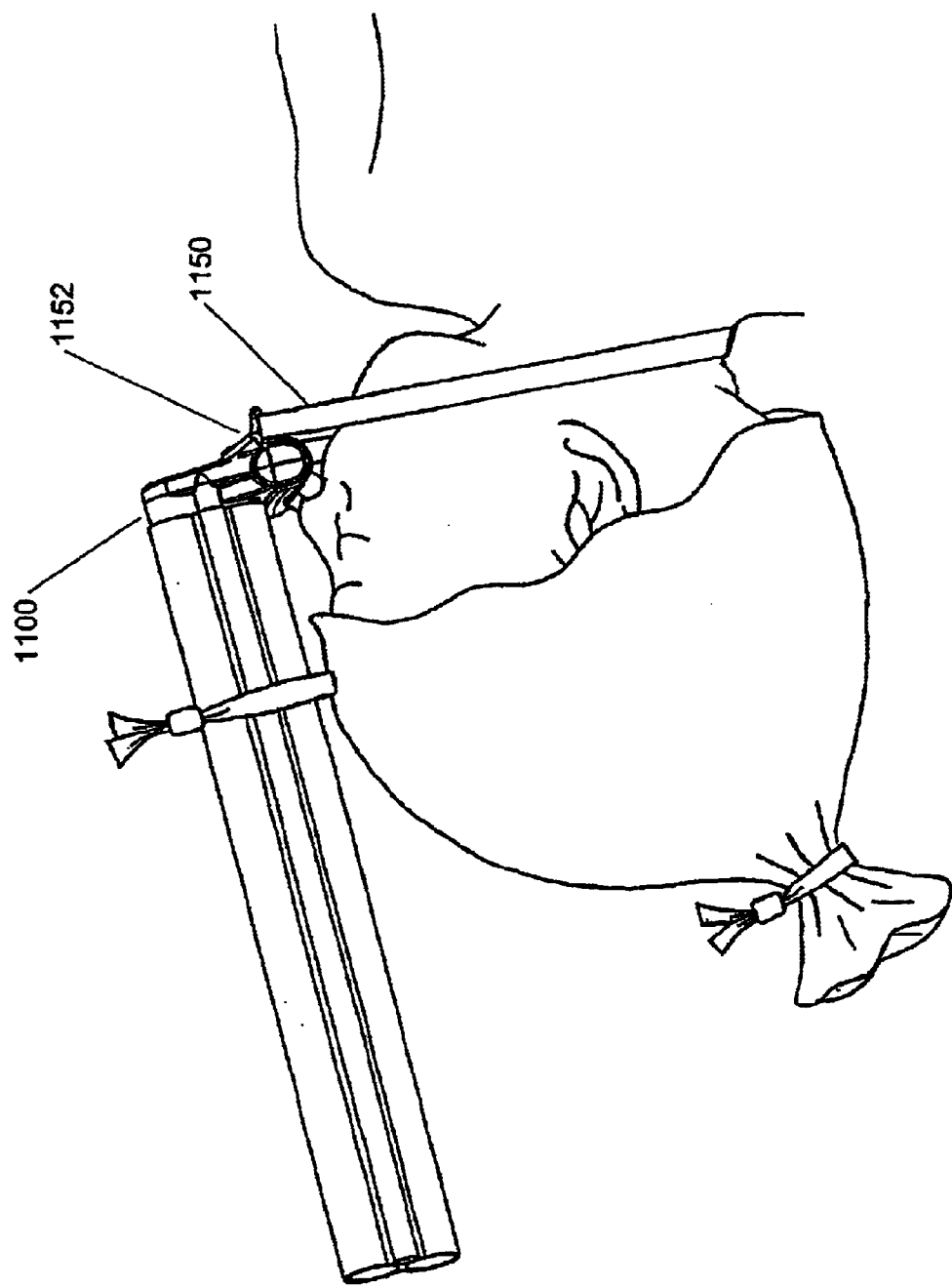
FIG. 10 is a side view of the cannula in use on a neonate.

Referring now particularly to FIGS. 9 and 10 we see that a nasal cannula 1100 is secured at its base to the back of a neonates head using strap 1150. The strap connects at the base of the neonates skull on the back of the neck. It connects to the cannula 1100 by way of a sliding strap 1152. This strap is secured by way of clips to the hard plastic body 1138 allowing the securing strap 1150 substantial relative movement with respect to the cannula 1100 as the neonate twists its head while providing adequate restraining force directly on the cannula 1100 without any twisting of the cannula 1100. In one embodiment this is accomplished by a plastic, e.g. acetal, sliding strap which engages into sliding clips on the outer face of the cannula. The strap, which is formed of TEFLON® material, is adjustably attached to the neck strap 150 to allow the tension to be adjusted to a comfortable level. Alternatively a sliding loop could be employed.

Full Face Mask

Referring to FIGS. 11 to 13 and 18 a number of further embodiments are illustrated particularly relating to full face masks. Similarly to the preceding embodiments in FIG. 18 the mask 1200 is attached to headgear around the head of a patient with a sliding strap 1202. which is formed of TEFLON® material. The strap engages through a channel 1201 moulded into the mask 1200.

Figure 11:
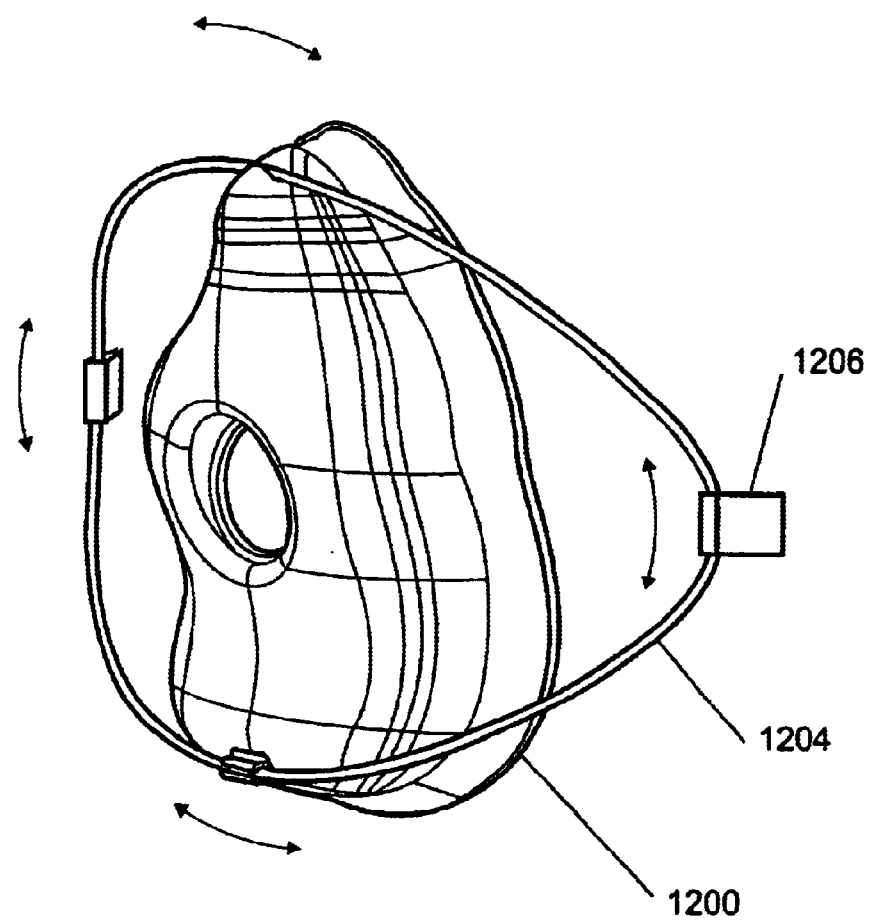
FIG. 11 is a perspective view of the full face mask with sliding loop.
Figure 12:
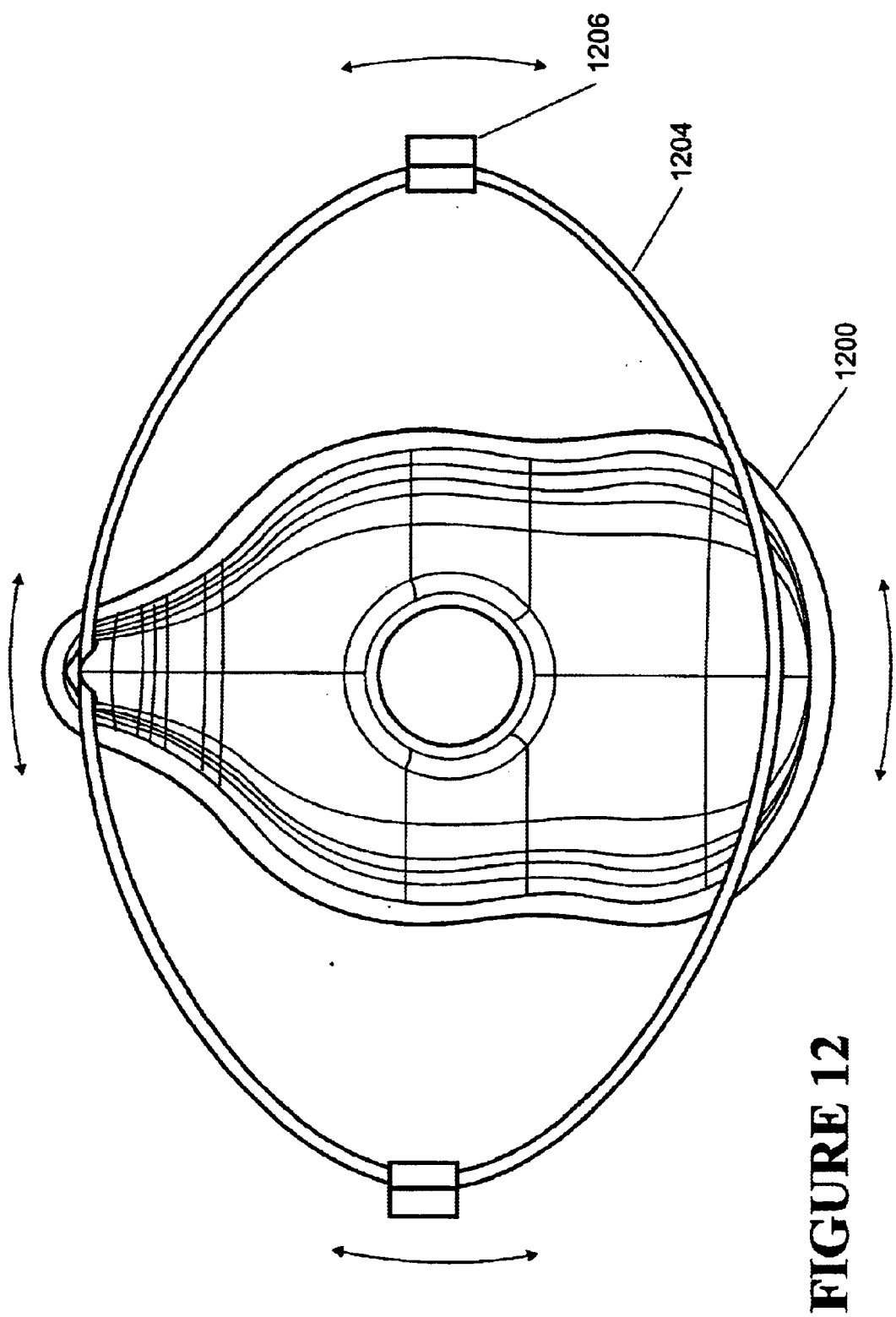
FIG. 12 is a front view of the full face mask with sliding loop.
Figure 13:
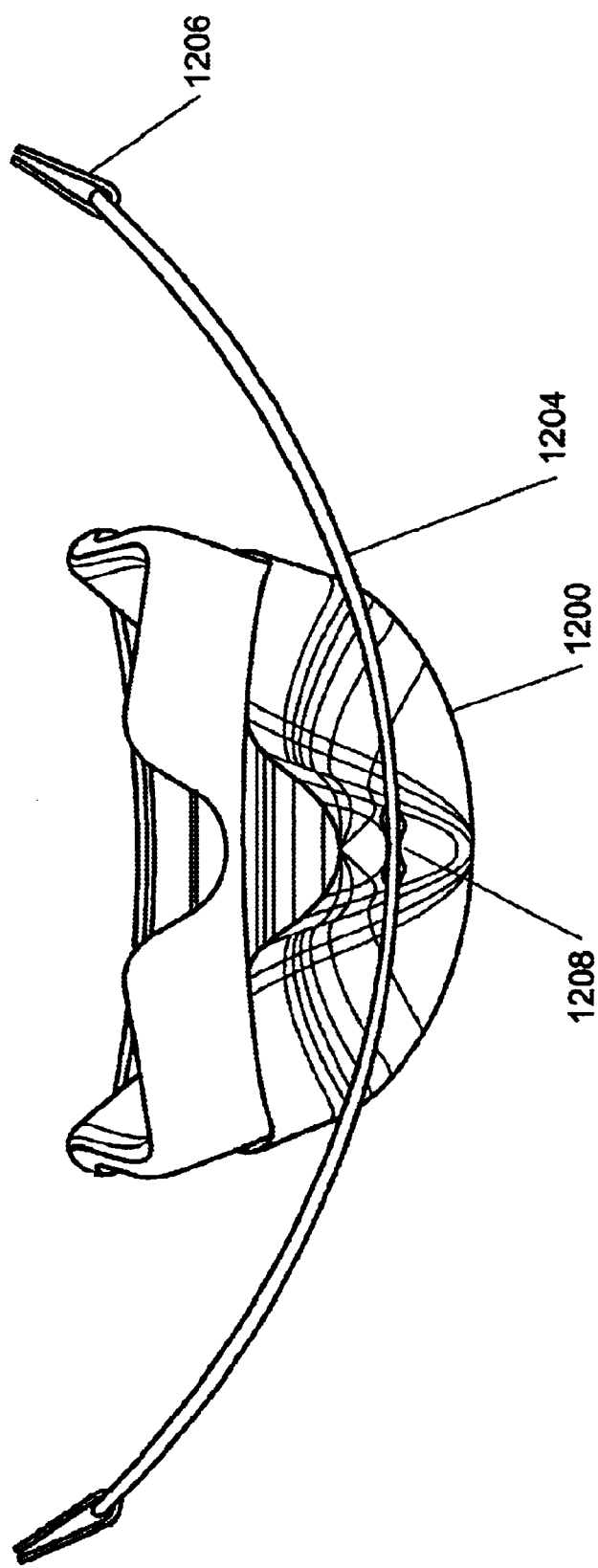
FIG. 13 is a top view of the full face mask with sliding loop.

Alternatively as seen in FIGS. 11 to 13 the mask 1200 is attached to the headgear with a sliding loop 1204. The loop engages with the headgear through loops 1206 which are formed of VELCRO® material and to the mask 1200 through clips 1208.

A further variation of the fill face mask embodiment is shown in FIGS. 19 to 23 Referring to the drawings, a mask 1602 in accordance with the present invention comprises a rigid or semi rigid shell 1603 which supports two short tubes 1604, 1605 and a flexible seal 1606.

Figure 20:
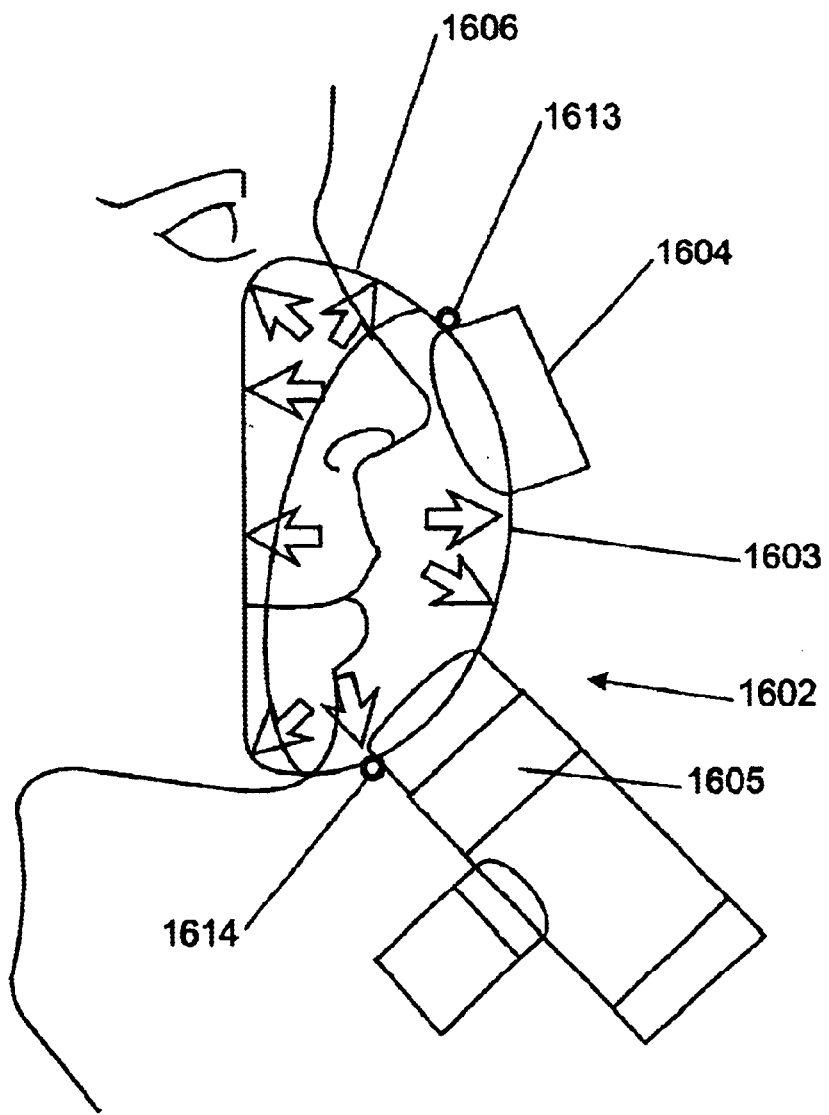
FIG. 20 shows a side view of the mask of FIG. 19, FIG. 21 and 22 are plan views of the front and rear sides respectively of a seal incorporated in the mask of FIG. 19.

The shell 1603 is domed and is dimensioned so as to extend from about the midpoint of the nose to below the mouth of a user, as shown in FIG. 20. The masks may of course be produced in a range of sizes to suit users from infants to large adults. Preferably, the shell 1603 is made of a lightweight transparent plastic material, and the two tubes 1604, 1605 are formed integrally with the shell.

The end of each tube 1604, 1605, attached to the shell 1603 extends through the shell and terminates as a short rim on the interior of the shell. These rims form attachment points for the seal 1606 as hereinafter described.

In use, the end of the inlet hose from an air or air/oxygen or oxygen supply is push fitted over the tube 1604 and secured in any suitable manner. A threshold resistor exhaust valve is fitted into the tube 1605; valves of this type are known and are used to regulate the release of expired gases from the mask so that a suitable over pressure is maintained in the mask. Alternatively the mask pressure could be regulated by varying the gas supply. Similarly expiratory gases might be vented through a simple aperture, an expiratory conduit.

Figure 21:
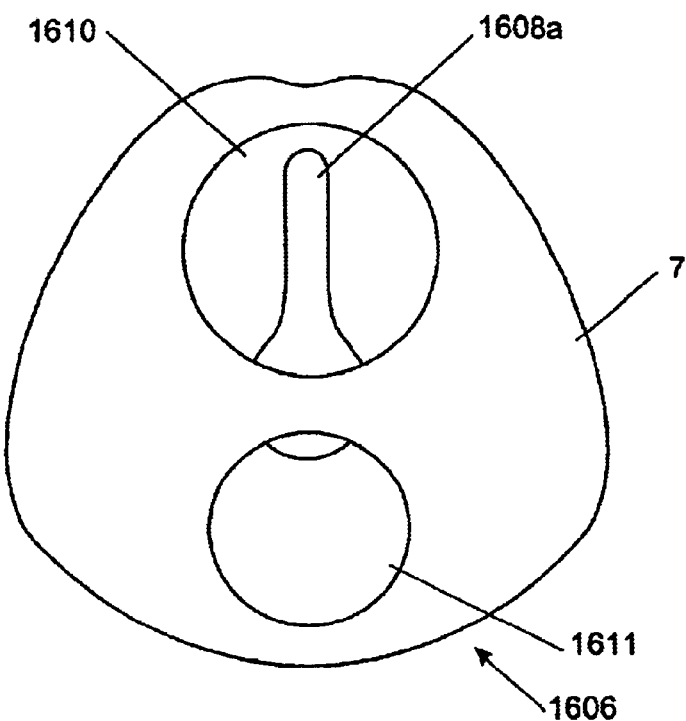
Figure 22:
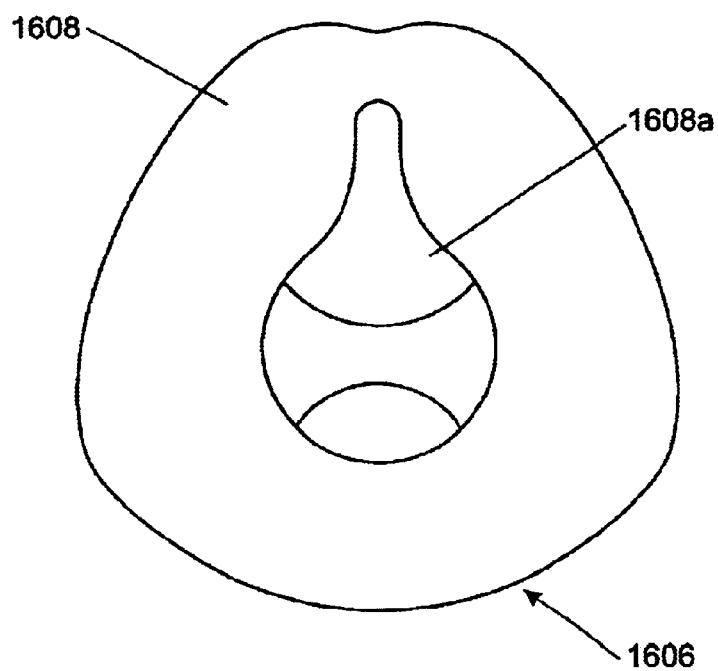

Referring in particular to FIGS. 21 and 22, the seal 1606 is a one-piece spheroid and may be made from any suitable gas tight, tough, flexible material which does not irritate the human skin on contact. The seal material must be very thin (typically 0.1–0.3 mm thick) so that it moulds easily to the contours of the face. Silicone rubber has been found to be a suitable material. The seal 1606 is larger overall than the internal dimensions of the shell 1603, so that in use the edges of the seal extend beyond the mask as shown in FIG. 20.

The seal 1606 is not permanently secured to the shell 1603, but simply is press fitted into the shell 1603:—the portion 7 of the seal wall is formed with a pair of apertures 16, 16 which correspond in position and size to the tubes 1604, 1605 and are press fitted over the interior rims of these tubes on the inner surface of the shell 1603. The edges of the apertures 16, 16 are thickened to form a strong elastic rim for a tight fit against the rims of the tubes 1604, 1605. In use, gas (e.g. air or oxygen or an air/oxygen mix) is supplied to the interior of the mask through the tube 1604 at above atmospheric pressure. The gas pressure presses the portion 1607 of the seal against the interior of the shell 1603, and pushes the opposite portion 1608 of the seal outwards into contact with the face of a user, as shown in FIG. 20, in which the solid arrows indicate the pressure applied to the seal 1606 by the air inside the mask. The portion 1608 has a keyhole shaped cutout 1608a through which the nose and mouth of the user extend through the seal 1606 into the interior of the mask. The edges of the cut out 1608a are of extremely thin material (i.e. even thinner than the remainder of the seal 1606) and at preformed so that they contour the nose/cheek bones/mouth/jaw of the user. The spherical shape of the seal 1606 means that when the mask is in use, not only the edges of the cut out 1608a, but also the surrounding curved walls of the seal, press against the user's face. The curved shape of the seal means that the seal can effectively "roll" against the user's face without losing sealing contact.

Since the seal 1606 is very flexible, the seal 1606 conforms readily to the contours of the user's face and forms an effective seal whilst applying a relatively light and uniform pressure to the face. The rigid or semi rigid material of the shell 1603 provides support for a major proportion of the seal, as shown in FIG. 20, but nowhere is pressed tightly into contact with the user's face, since the actual seal between the mask and the face is formed by the seal 1606. This is in contrast to conventional mask designs, where, when the mask is in use, the strapping pulls the mask tightly against the user's face to form an effective seal.

The seal 1606 can be removed and replaced quickly and easily; the remainder of the mask can be sterilized for reuse.

The above described mask can be supported by conventional strapping (not shown) secured to the edges of the shell 1603 in known manner. However, additional advantages are obtained if the mask is supported on the user by the novel harness system shown in FIGS. 19 and 23.

Figure 19:
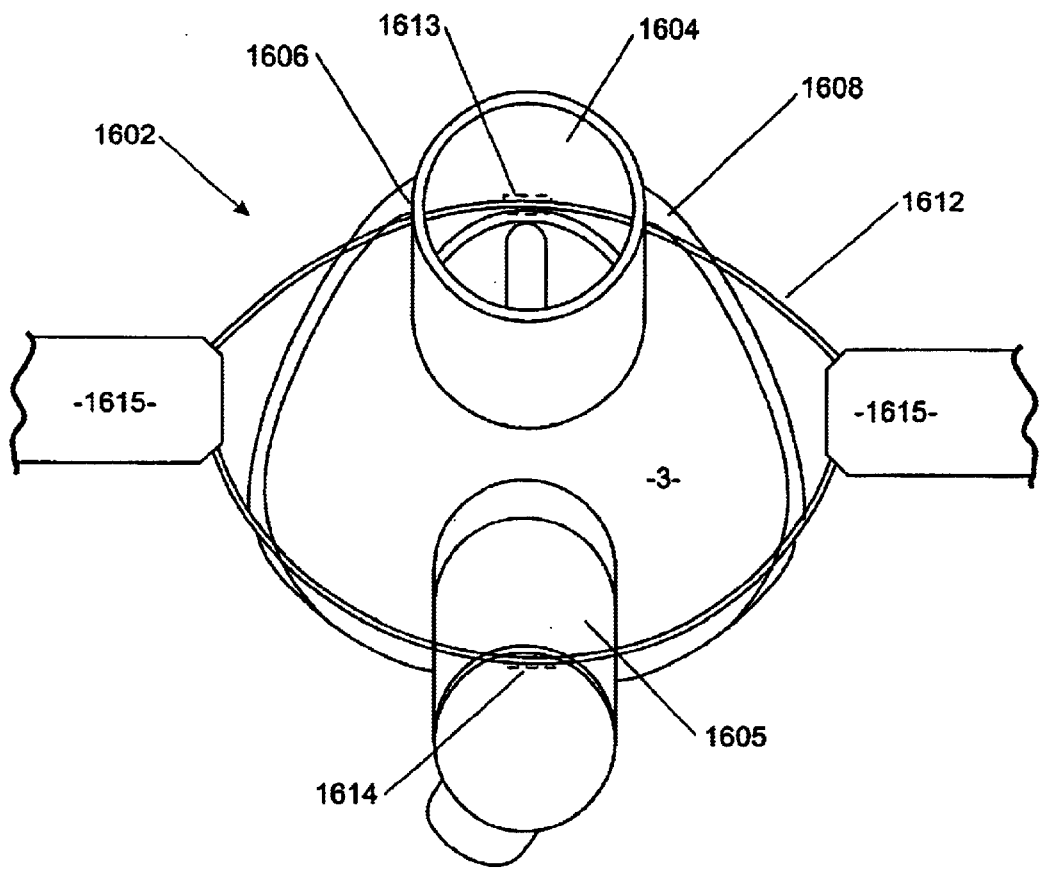
FIG. 19 shows a front view of the Her variations in the full face mask of the present invention.
Figure 23:
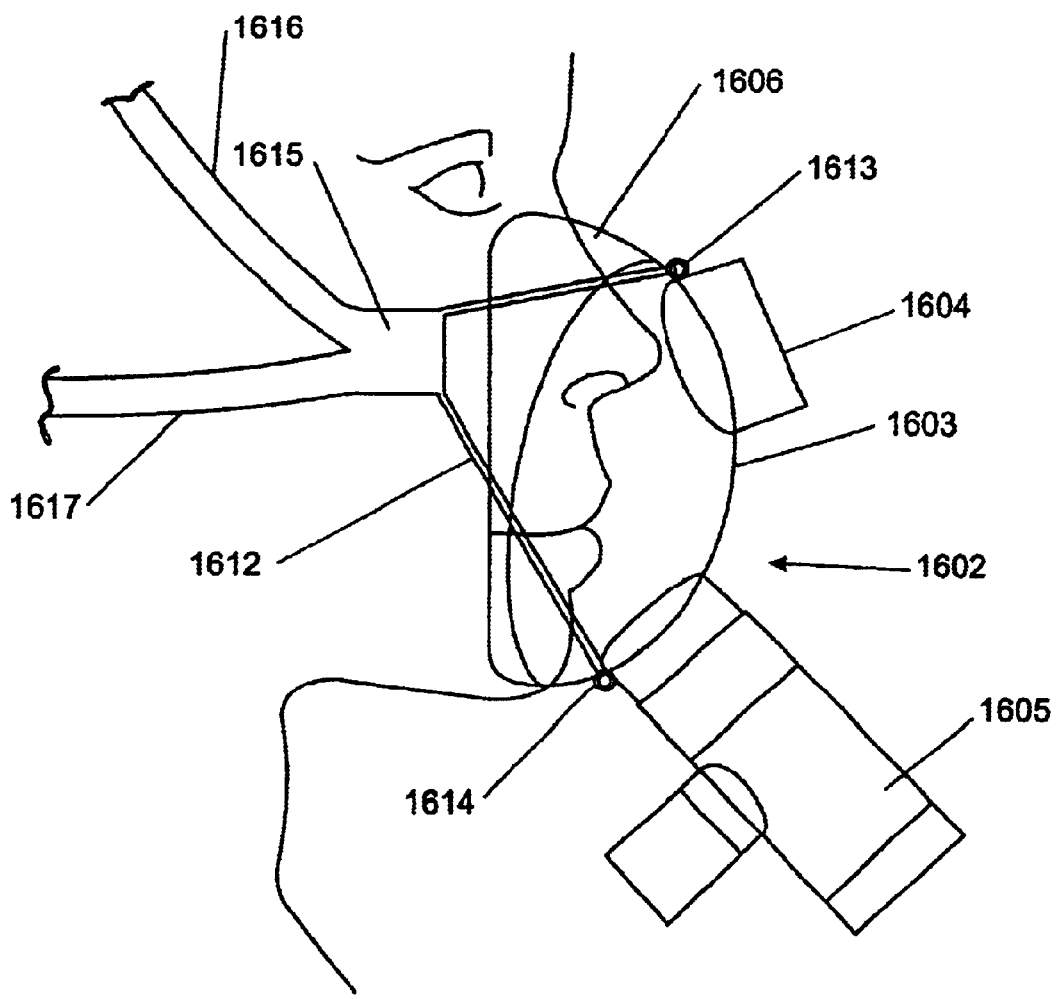
FIG. 23 shows a side view of the mask of FIG. 19 in use.

Referring in particular to FIGS. 19 and 23, the mask harness system comprises a loop of low friction, tough, fatigue resistant cord 1612 (e.g. Kevlar or nylon) which passes through a pair of channels 1613, 1614 respectively at the top of and bottom of the outer surface of the shell; the channel 1613 is located above the tube 1604 and the channel 1614 below the tube 1605. The cord 1612 can slide freely through the channels 1613 and 14. At each side of the mask, a strap 1615 is mounted on the cord 1612; each end of the strap 1615 incorporates a tube (not visible) of low friction material through which the cord 1612 can slide freely.

As shown in FIG. 23 only, the strap 1615 is divided into two portions 1616, 1617 at each side, to pass around the users head in known manner. The strap 1615 is provided with known length adjustment means (not shown), so that the length of the strap 1615 can be adjusted to provide a secure but comfortable fit on the user's head. The strap 1615 may be made of, or incorporate, elastic material and preferably is fastened adjacent one side of the mask using a Velcro (Reg. T.M.) fastener (not shown).

The above described mask harness system provides for some freedom of movement about three mutually perpendicular axes without breaking the seal between the seal 1606 and the user's face. The fact that the cord 1612 can slide freely in the channels 1613 and 1614 and on the strap 1615 allows the mask to move relative to the user rotating about a vertical axis or about a horizontal axis, and also to translate in the vertical axis (i.e. equivalent to pitch, yaw and roll, in aeronautical terms). It follows that the mask is self centering on the user's face, and accommodates movement of the gas supply line and of the user, without affecting the efficiency of the seal. It will be appreciated that this greatly improves not only the efficiency, but also the comfort, of the mask.

Mouthpiece

Figure 14:
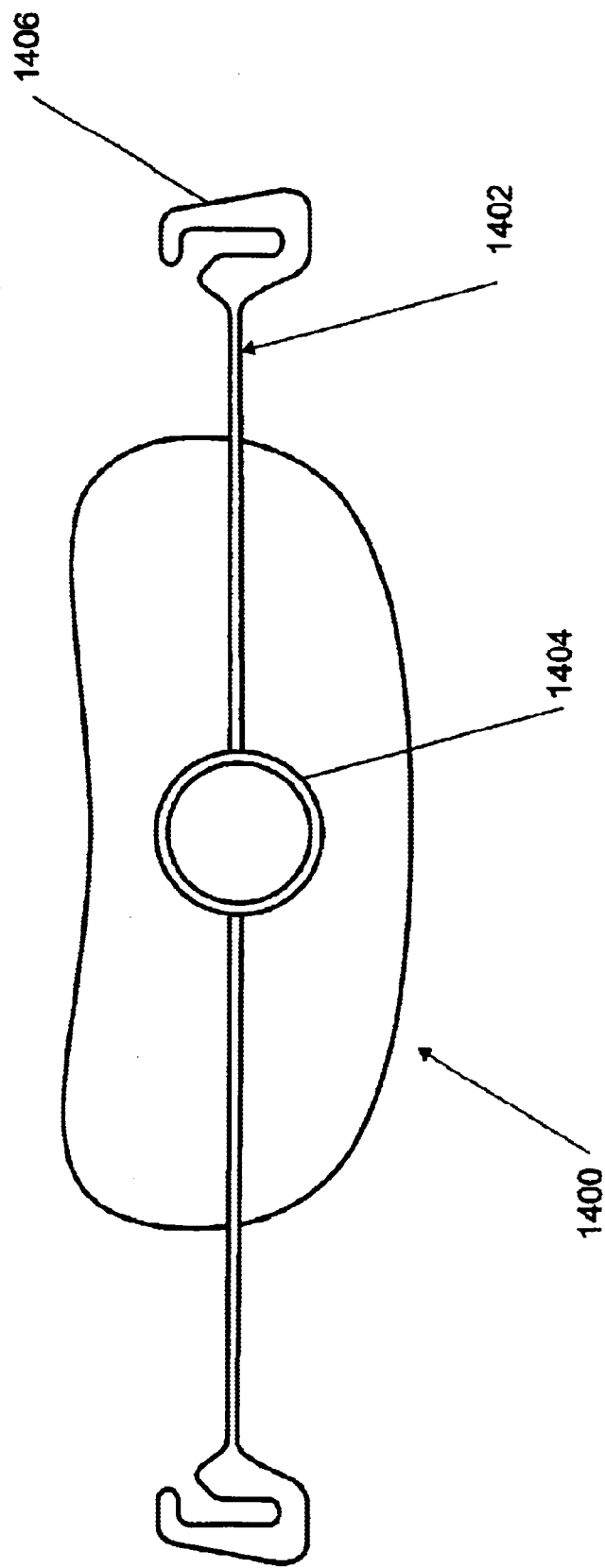
FIG. 14 is a front view of the single sliding strap on the mouthpiece.
Figure 15:
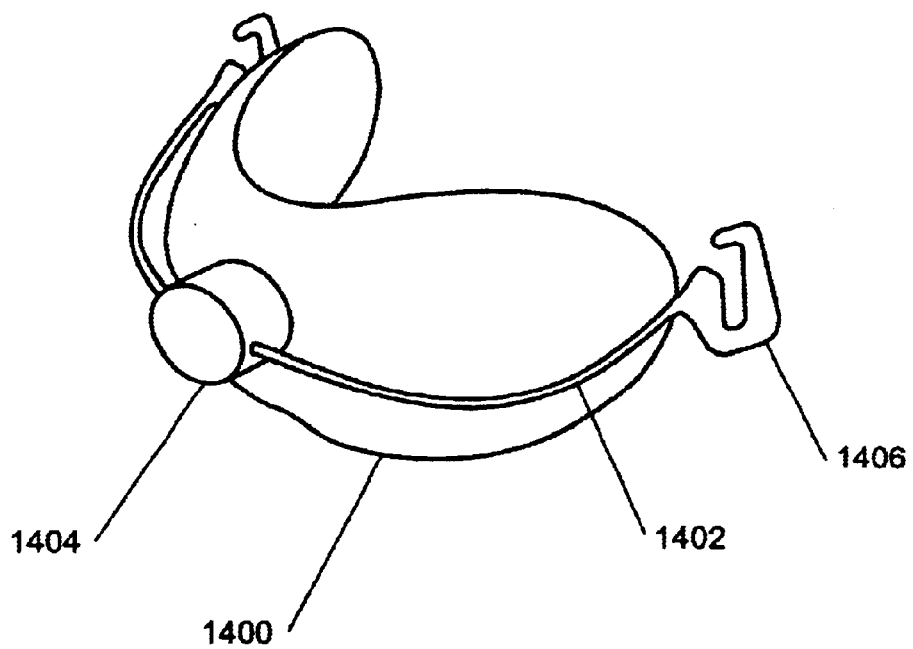
FIG. 15 is a perspective view of the single sliding strap on the mouthpiece.
Figure 16:
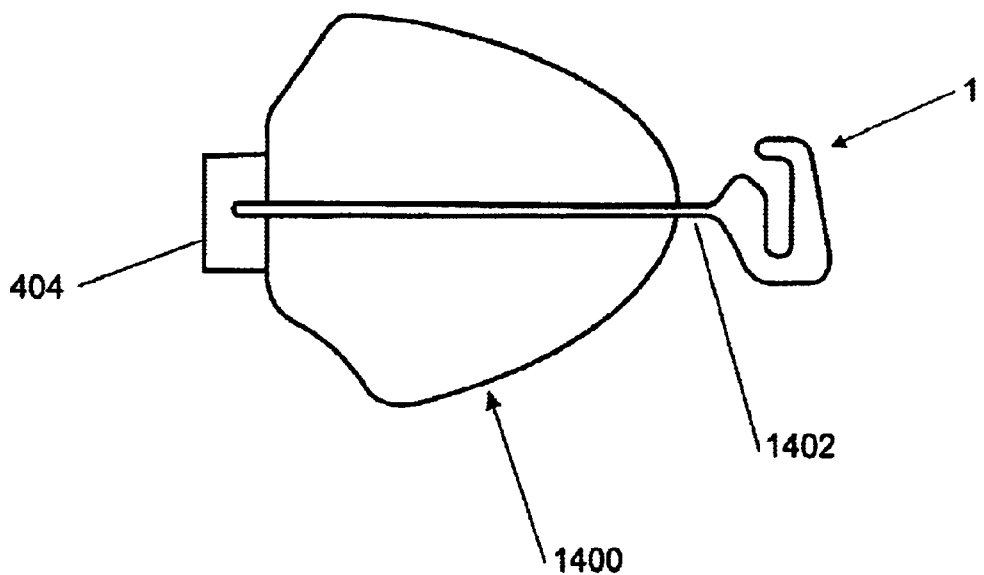
FIG. 16 is a side view of the single sliding strap on the mouthpiece.
Figure 17:
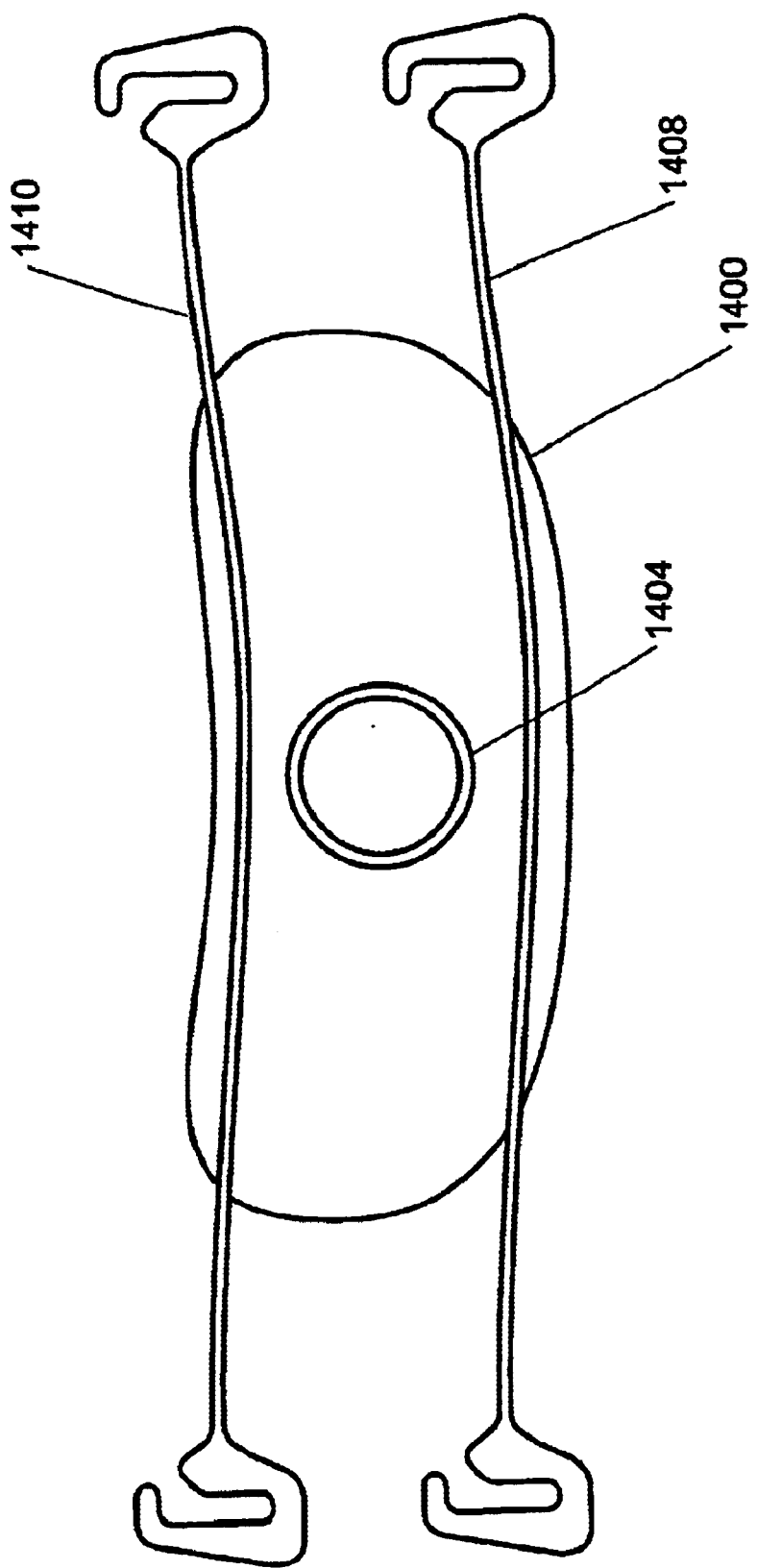
FIG. 17 is a front view of the double sliding strap on the mouthpiece.
Figure 18:
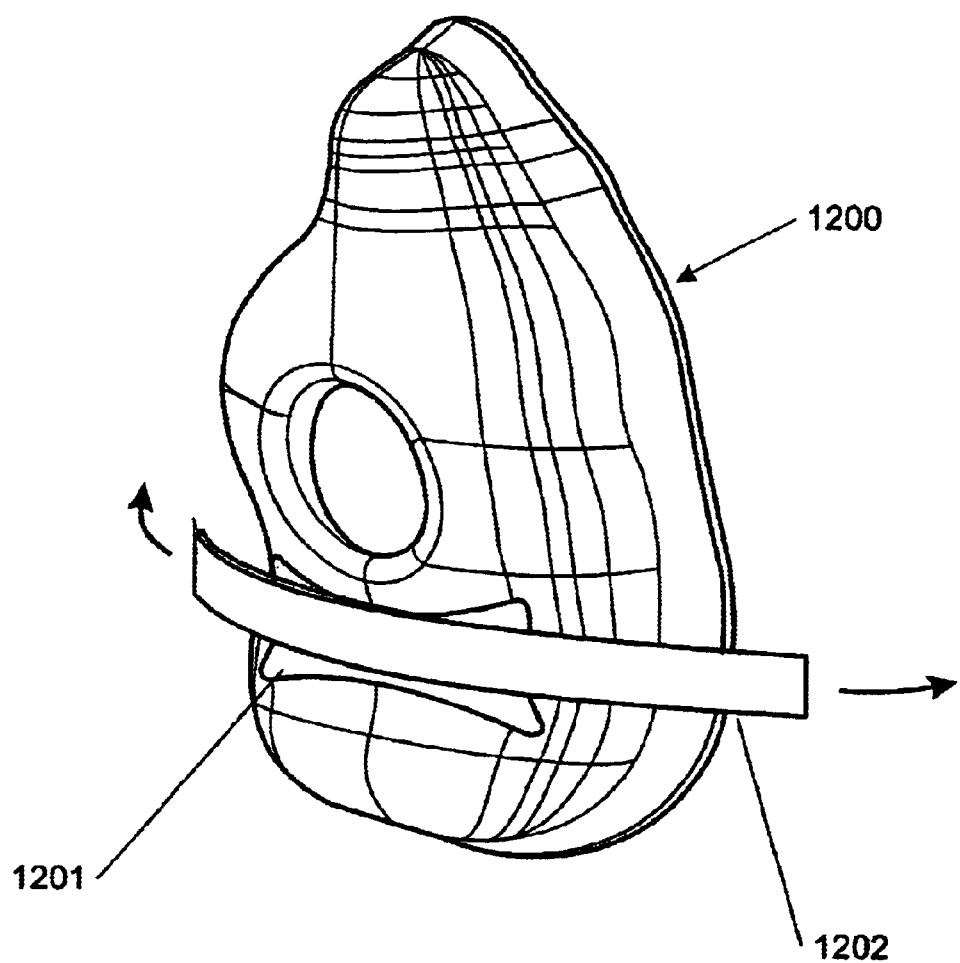
FIG. 18 is a perspective view of the sliding strap for the full face mask.

Referring to FIGS. 14 to 16 a mouthpiece 1400 is shown employing embodiments of the present invention. The mouthpiece 1400 engages with sliding strap 1402 through a channel through the inlet 1404 of the mouthpiece 1400. Again as with the preceding embodiments the strap 1402 engages to the headgear through clips 1406 at each end. In FIG. 17 two straps 1408, 1410 attach to the mouthpiece 1400 either side of the inlet 1404 in a further alternative. The mouthpiece employed could otherwise be as described in our European Patent Application No. 1163924 or other mouthpieces as would be contemplated by one skilled in the art.

It will be appreciated that numerous other interfaces for example E.T (endotracheal) tubes might also be used in conjunction with the present invention.

What is claimed is:

1. A device for delivering a supply of gases to a user comprising:

a patient interface, adapted to be in fluid communication with said supply of gases, and said user in at least a correct orientation and position on said user, headgear adapted to attach to or around the head of said user, a member connected to said patient interface, and a sliding connection between said member and said headgear.

2. A device as claimed in claim 1 wherein said member comprises a loop slidable on, through, with or adjacent said patient interface and slidable on, through, with or adjacent said headgear.

3. A device as claimed in claim 1 or 2 wherein said member is connected to said patient interface at at least two points.

4. A device as claimed in claim 2 wherein said loop comprises a continuous loop of nylon filament.

5. A device as claimed in claim 1 wherein said patient interface is a mask.

6. A device as claimed in claim 1 wherein said patient interface is a nasal mask.

7. A device as claimed in claim 1 wherein said patient interface is a full face mask.

8. A device as claimed in any one of claims 5 to 7 wherein said mask comprises or includes a body portion having an inlet receiving said supply of gases, and sealing means attached to or integrated with said body portion said sealing means adapted to seal against the facial contours of said user.

9. A device as claimed in claim 8 where said member is adapted to allow said headgear substantial movement with respect to said mask, while still providing compressive force on said sealing means to ensure said supply of gases is delivered to said user without significant leakage.

10. A device as claimed in claim 1 wherein said patient interface is a nasal cannula.

11. A device as claimed in claim 1 wherein said patient interface is a mouthpiece.

12. A device as claimed in claim 1 wherein said patient interface is an endotracheal tube.

13. In a CPAP system for delivering gases to a user with a pressurised source of gases, a conduit in fluid communication with said pressurised source adapted to convey said gases, a patient interface in fluid communication with said conduit in use delivering said gases to said user, headgear attached to or around the head of said user and a structure connecting said patient interface with said headgear, the improvement comprising a sliding connection between said structure and said headgear.

14. In a CPAP system as claimed in claim 13 the improvement further comprising that said system further comprises a humidifier to variably humidify said gases.

15. In a CPAP system as claimed in claim 13 the improvement further comprising said member being slideably connected to said patient interface.

16. In a CPAP system as claimed in claim 13 wherein said member comprises a loop where said loop is adapted to slide on, through, with or adjacent said patient interface and adapted to slide on, through, with or adjacent said headgear.

17. A device for delivering a supply of gases to a user comprising or including:
   a patient interface, adapted to be in fluid communication with a supply of gases, and said user in at least a correct orientation and position on said user, and
   headgear attached to the head of a user, and
   at least a partial loop adapted to pass across the face of a user restraining movement of said patient interface with respect to said headgear.

18. A device as claimed in claim 17 wherein said loop passes over and slidingly engages with said patient interface.

19. A device as claimed in claim 17 wherein said loop passes at least partially through and slidingly engages with said patient interface.

20. A device as claimed in claim 18 or 19 wherein said loop slidingly engages with said headgear.

21. A mask which includes a rigid or semi rigid shell provided with a sliding support harness for securing the mask over a user's face, and a flexible seal; the shell being provided with inlet means for a gas supply and a mounting for an outlet; the flexible seal being a push fit inside the shell and dimensioned and arranged such that when pressurized gas is supplied through the inlet means, the seal is pushed outwards against the interior of the mask and against the user's face.

22. A mask as claimed in claim 21 wherein the support harness comprises a loop of low friction material which can slide freely through channels formed in the shell and relative to straps provided for securing the mask around a user's head.

* * * * *

UNITED STATES PATENT AND TRADEMARK OFFICE
CERTIFICATE OF CORRECTION

PATENT NO. : 6,701,926 B2  Page 1 of 1
DATED : March 9, 2004
INVENTOR(S) : Gregory James Olsen et al.

It is certified that error appears in the above-identified patent and that said Letters Patent is hereby corrected as shown below:

Column 3,
Line 61, "Her" should be -- further --

Column 5,
Line 42, "art In" should be -- art. In --
Line 60, "within We" should be -- within the --

Column 6,
Line 15, "while sill" should be -- while still --
Line 48, "1202. which" should be -- 1202, which --
Line 56, "fill face" should be -- full face --

Column 7,
Line 44, "and at" should be -- and are --

Signed and Sealed this

Seventeenth Day of August, 2004

JON W. DUDAS
*Acting Director of the United States Patent and Trademark Office*